(12) United States Patent
Fridman et al.

(10) Patent No.: US 10,258,793 B2
(45) Date of Patent: Apr. 16, 2019

(54) ARTIFACT CONTROL AND MINIATURIZATION OF THE SAFE DIRECT CURRENT STIMULATOR FOR NEURAL PROSTHESES

(71) Applicant: The Johns Hopkins University, Baltimore, MD (US)

(72) Inventors: Gene Yevgeny Fridman, Baltimore, MD (US); Charles Coleman Della Santina, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 76 days.

(21) Appl. No.: 15/431,272

(22) Filed: Feb. 13, 2017

(65) Prior Publication Data

US 2017/0203099 A1    Jul. 20, 2017

Related U.S. Application Data

(63) Continuation of application No. 14/366,870, filed as application No. PCT/US2012/070860 on Dec. 20, 2012, now Pat. No. 9,572,979.

(Continued)

(51) Int. Cl.
*A61N 1/32* (2006.01)
*A61N 1/30* (2006.01)
(Continued)

(52) U.S. Cl.
CPC ............... *A61N 1/303* (2013.01); *A61N 1/20* (2013.01); *A61N 1/32* (2013.01); *A61N 1/325* (2013.01); *A61N 1/3605* (2013.01); *A61N 1/44* (2013.01)

(58) Field of Classification Search
CPC ...... A61N 1/303; A61N 1/3605; A61N 1/325; A61N 1/44
See application file for complete search history.

(56) References Cited

U.S. PATENT DOCUMENTS 5,476,481 A * 12/1995 Schondorf ............... A61N 1/32
607/2
7,896,874 B2    3/2011 Young et al.
(Continued)

FOREIGN PATENT DOCUMENTS

CN        101056593 A        10/2007
CN        101138528 A         3/2008
(Continued)

*Primary Examiner* — Amanda K Hulbert
*Assistant Examiner* — Natasha Patel
(74) *Attorney, Agent, or Firm* — Venable LLP; Henry J. Daley (57) ABSTRACT

An embodiment in accordance with the present invention provides a device and method to deliver direct ionic current safely to target neural tissue, while also eliminating interruptions in the output of the device that can result from the non-ideal operation of the valves used to control the current flow in the device. The device includes two valve-operated systems that work in tandem. The first and second current producing systems are configured to be used together in order to eliminate the periodic interruptions in current flow. In use, one system drives current through the target tissue, while the other system closes all of the valves first and then opens its valves in sequence. This intermediate step of closing all of the valves prevents unintended current shunts through either system. The device also includes two conductors to direct the flow of direct current into the target tissue.

19 Claims, 6 Drawing Sheets

Related U.S. Application Data

(60) Provisional application No. 61/577,821, filed on Dec. 20, 2011.

(51) Int. Cl.
*A61N 1/44* (2006.01)
*A61N 1/20* (2006.01)
*A61N 1/36* (2006.01)

(56) References Cited

U.S. PATENT DOCUMENTS

| | | |
|---|---|---|
| 2003/0125768 A1 | 7/2003 | Peter |
| 2006/0136007 A1 | 6/2006 | Mickle et al. |
| 2011/0160798 A1 | 6/2011 | Ackerman, Jr. et al. |
| 2011/0166627 A1* | 7/2011 | Carter ................. A61N 1/0541 607/57 |
| 2013/0125768 A1 | 5/2013 | Shi et al. |

FOREIGN PATENT DOCUMENTS

| WO | WO-2010/025514 A1 | 3/2010 |
|---|---|---|
| WO | WO-2011-088130 A2 | 7/2011 |

* cited by examiner

ARTIFACT CONTROL AND MINIATURIZATION OF THE SAFE DIRECT CURRENT STIMULATOR FOR NEURAL PROSTHESES

CROSS REFERENCE TO RELATED APPLICATIONS

This application is a continuation of U.S. patent application Ser. No. 14/366,870, filed on Jun. 19, 2014, which is a 35 U.S.C. § 371 U.S. national entry of International Application PCT/US2012/070860, having an international filing date of Dec. 20, 2012, which claims the benefit of U.S. Provisional Application No. 61/577,821, filed Dec. 20, 2011, the entire contents of which are hereby incorporated by reference.

GOVERNMENT SUPPORT

This invention was made with government support under NIH R01DC009255 awarded by the National Institute of Health. The government has certain rights in the invention.

FIELD OF THE INVENTION

The present invention relates generally to neural stimulation. More particularly, the present invention relates to a device and method for delivering DC current to target tissue.

BACKGROUND OF THE INVENTION

While effective in treating some neurological disorders, neural prostheses are limited because they can excite neurons but not efficiently inhibit them. Direct current (DC) applied to a metal electrode in contact with neural tissue can excite or inhibit neural activity; however, DC stimulation is biologically unsafe because it causes electrochemical reactions at the metal electrode-tissue interface. To avoid these safety hazards, neural prostheses generally deliver alternating current (AC) pulses to evoke action potentials.

While cochlear and retinal prostheses use AC pulses to encode sensory information by modulating firing rate of the afferent fibers above their spontaneous activity, other neural prosthesis applications have substantial difficulties achieving effective treatment with excitation alone. A prosthesis to assist micturition, for instance, requires both excitation of sacral nerves to activate the detrusor muscle and simultaneous inhibition of lumbar nerves to relax the urethral sphincter. For proper balance as well, inner ear vestibular afferent fibers require not only excitation to encode head motion toward the stimulated side of the head, but also inhibition to encode head motion away from it. In restoring normal physiology, therefore, the ability for a neural prosthesis to both inhibit and excite neurons would be useful. Furthermore, several disorders characterized by high neural firing rates such as tinnitus, chronic pain, and epilepsy could be effectively treated by prostheses capable of neural inhibition. Gradual modulation of extracellular potential rather than evoking or inhibiting spikes could further extend the capabilities of neural prostheses to treating disorders such as autism by addressing excitatory vs. inhibitory imbalance, and DC potential support to treat strial hearing loss.

At low amplitudes, DC can achieve graded control of neural activity by altering the extracellular electric field near the electrode. By altering the electric field, DC modulates neural firing thresholds, increasing or decreasing the likelihood of spike initiation. At higher DC amplitudes, cathodic current excites neurons, while anodic current inhibits them. DC stimulation that does not produce electrochemical reactions at the electrode-saline interface could enable more versatile treatments of neurological disorders than what is currently possible.

Figure 1A:
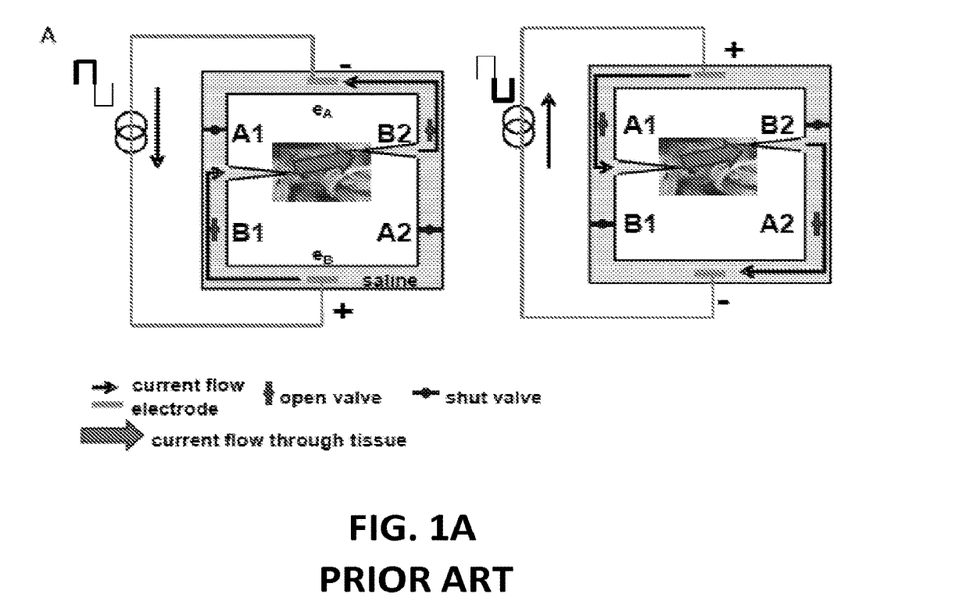
FIG. 1A illustrates a schematic diagram of the fundamental concept behind providing direct current stimulation to the tissue, while delivering alternating current to the metal electrodes within the device. Two states of the same system are shown.
Figure 1B:
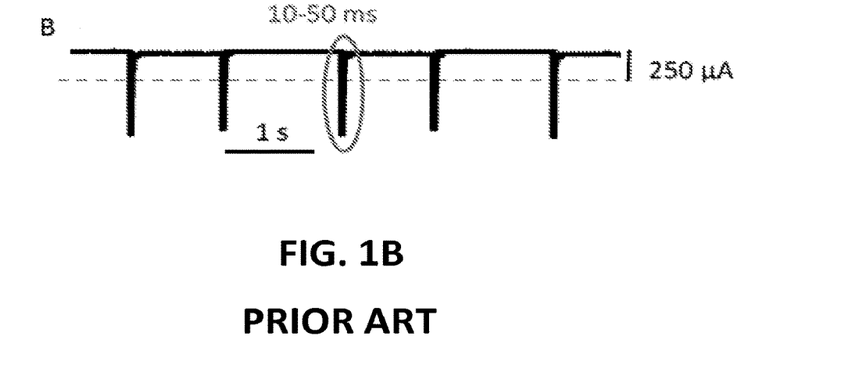
FIG. 1B demonstrates the periodic interruptions that occur at the system output from the prototype of the device described in FIG. 1A. The interruptions occur at every phase transition of the alternating current and valve states.

A solution to the problem of DC stimulation safety is to direct the DC flow of ions into the target tissue by switching mechanical valves in phase with AC square waves applied to the electrodes, which are immersed in an ionic solution. This approach removes DC from the electrode-saline interface, while maintaining DC ionic current through the tissue. FIG. 1A shows the two potential states of the system. FIG. 1B shows the output of the fully-functioning SDCS as the valves operate in synchrony with AC delivered to the electrodes. One important aspect of this device is that it works in a bipolar configuration so that the ions flowing into one tube are replenished by the same types of ions flowing out of the other tube thus resulting in net zero ionic change in the tissue between the two tubes. This configuration addresses pH changes that could potentially be harmful to the neural tissue.

The fidelity of the DC signal is degraded by periodic interruptions in current flow due to non-ideal behavior of the mechanical valves used in the device, as illustrated in FIG. 1B. The interruptions occur because ionic current bypasses the tissue when the valves are temporarily and simultaneously either open or closed during open-to-close and close-to-open transitions. For example, if B2 and A2 are both closed during a transition, no current will flow through the tissue. The duration of the interruptions depends on the speed of the valve transitions from open-to-close and from close-to-open states. Any interruption in the DC current flow however will cause the undesirable volley of neural activity in the target neurons.

It would therefore be advantageous to provide a method to remove the interruptions in the ionic direct current flow.

SUMMARY OF THE INVENTION

The foregoing needs are met, to a great extent, by the present invention, wherein in one aspect, a device for delivering direct current includes a first set of two electrodes and a second set of two electrodes configured to receive alternating current. The device also includes a first set of valves. The first set of valves includes a first and second pair of valves. The device also includes a second set of valves. The second set of valves includes a third and fourth pair of valves. The first and second sets of valves are configured to be opened and closed and are further configured to switch in phase with the alternating current applied to the first electrode and the second electrode. A tube is filled with conductive material and configured to direct the direct current flow of ions into target tissue. Additionally, the device is configured such that the first set of valves is closed when the third and fourth pairs of valves are being opened and the second set of valves is closed when the first and second pairs of valves are being opened.

In accordance with another aspect of the present invention, two systems work in tandem. In the arrangement described in the present invention, one system controls the ionic current system output to the tissue, while the second system undergoes valve transitions without affecting the device output. After the valves transition states in the second system, control of the device output switches electronically from the first system to the second thus allowing the first system to switch its valves without affecting the device output. In this way, the smooth ionic current output of the device is maintained independent of the valve transition speed.

In accordance with an aspect of the present invention, the conductor takes the form of a tube defining a hollow lumen extending therethrough. The hollow lumen of the tube is filled with a conductive material, and the conductive material is an ionic solution or an ionic hydrogel. The system further includes a housing having multiple layers. Each one of the layers of the housing contains one of the electrodes or the first set of valves and the second set of valves. Layer 1 of the housing contains channels filled with an ionic solution or electrolytic gel to conduct ionic current flow. Layer 2 encloses and protects layer 1 and provides openings through which the channels in layer 1 can be connected or disconnected to control the ionic current flow through them. Layers 3 and 4 add the ability to mechanically connect or disconnect the channels via the openings in Layer 2, forming the valves used to operate the device. The valves can take the form of mechanical valves, bridge rectifiers, or ionic diodes. Additionally, the mechanical valves can be actuated using Nitinol wire.

In accordance with another aspect of the present invention, a method for delivering direct current includes applying alternating current to electrodes immersed in an ionic solution. The method also includes closing a first set of valves and switching a second set of valves in sequence and in phase with the alternating current. Additionally the method includes directing the direct current flow of ions into a target tissue.

In accordance with yet another aspect of the present invention, the first set of valves includes a first and second pair of valves and the second set of valves comprises a third and fourth pair of valves. The first and second set of valves are configured to be opened and closed and are further configured to switch in phase with alternating current applied to the electrodes. A conductor is used to direct the direct current flow of ions into the target tissue. The conductor includes a tube defining an elongate inner lumen, and the elongate inner lumen of the tube is filled with a conductive material. The conductive material is an ionic solution or an ionic hydrogel. The method further includes closing the first set of valves when the third and fourth pair of valves are open, and closing the second set of valves when the first and second pairs of valves are open.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a device and method to deliver direct current to a target tissue, while also eliminating interruptions in current flow. Two systems are used in tandem to deliver uninterrupted current to the neural tissue via two conductors. The two conductors (a.k.a. Tube electrode) are used to direct the flow of ionic current from the device into the target tissue. The first and second current producing systems are configured to be used together in order to eliminate the periodic interruptions in current flow. In use, one system drives current through the target tissue, while the other system closes all of the valves first and then opens its valves in sequence. This intermediate step of closing all of the valves prevents unintended current shunts through either system.

Figure 2:
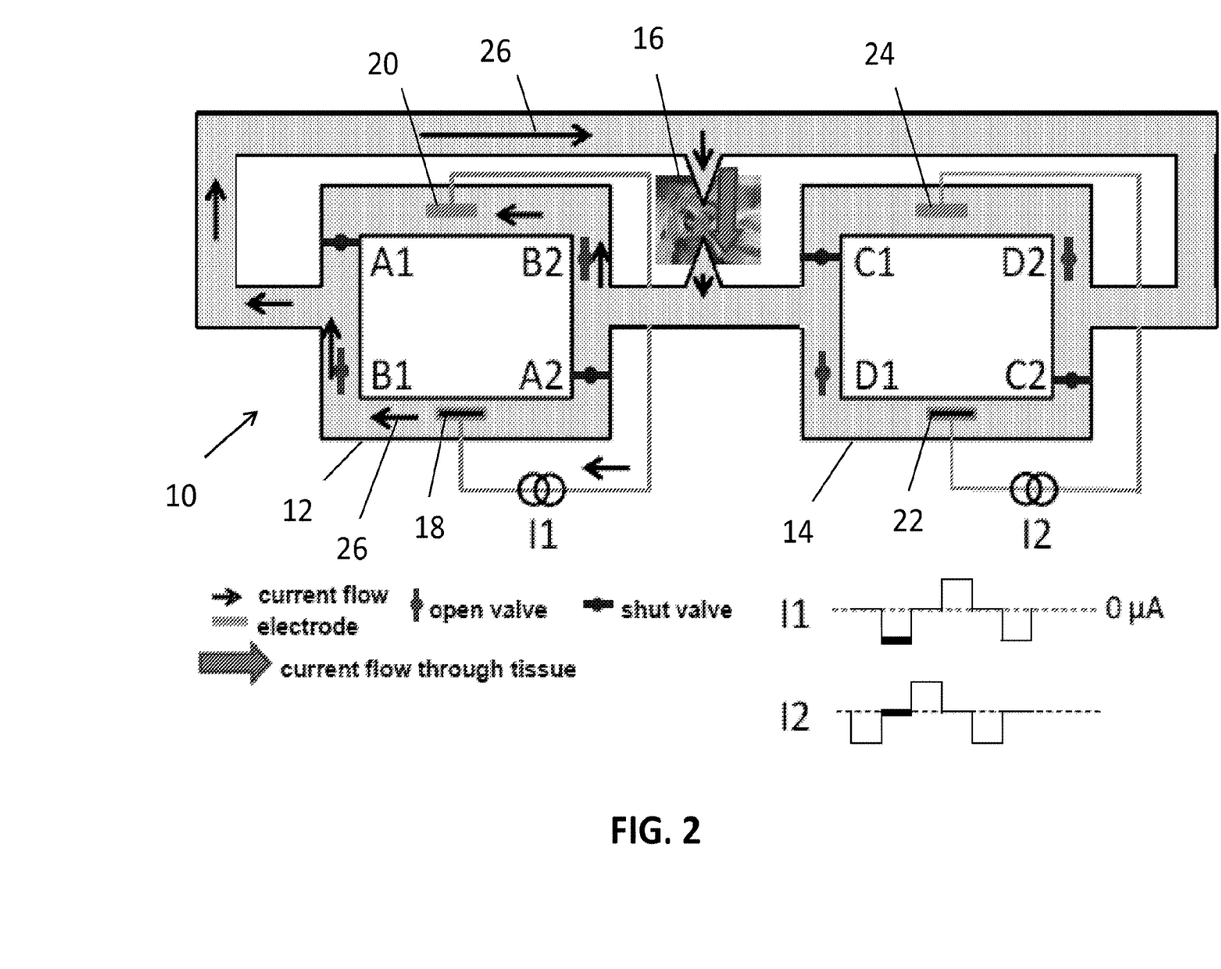
FIG. 2 illustrates a device for delivering direct current flow to target tissue and configured to eliminate current interruptions, according to an embodiment of the present invention.

FIG. 2 illustrates a device for delivering direct current flow to target tissue and is configured to eliminate current interruptions, according to an embodiment of the present invention. As illustrated in FIG. 2, the device 10 includes a left system 12 and a right system 14, both configured to deliver current to target tissue 16. The left system 12 includes a pair of electrodes 18, 20 and the right system 14 includes a pair of electrodes 22, 24. The electrodes 18, 20, and 22, 24 are configured to receive alternating current from current sources I1 or I2 respectively. After the electrical current enters either the left system or the right system it travels through a conductive material, such as saline, or any other suitable conductive material or solution known to one of skill in the art. The left system 12 includes valves A1, A2, B1, and B2, and the right system 14 includes valves C1, C2, D1, and D2. The valves can take the form of mechanical valves, other valve technology known to or conceivable by one of skill in the art. Additionally, the valves can be miniaturized using micro-electrical-mechanical miniaturization (MEMS) or other miniaturization technology. Valve A1 is always in the same state as valve A2, valve B1 is always in the same state as valve B2 and so on.

Additionally, FIG. 2 illustrates an example of flow of current 26 between electrodes 18 and 20 through the device 10 in order to deliver the current to the target tissue 16. In the example presented in FIG. 2, the electric ionic current 26 flows easily through any open valve, such as, for example in FIG. 2, valves B1, B2, D1, and D2 and not through the closed valves, such as indicated by valves A1, A2 and C1 and C2. As noted above, the device 10 uses a left system 12 and a right system 14. One system drives current through the tissue, while the other closes all valves first and then opens the next set of valves in sequence. Table 1, below, shows the states of the device 10 for different valve closures. The states are entered sequentially and repeat after S12. The state of the device is indicated in the left column. The asterisks (*) indicate a switch in the current source that is controlling the flow through the tissue from the previous state. "0" indicates that the valve is closed. "1" indicates that the valve is open. Current sources I1, I2 can either control flow from upper electrode to the lower electrode in each of the two systems, indicated by "+"; lower to upper electrode indicated by "−"; or be off, indicated by "0." It should also be noted that the direct current is delivered to the target tissue 16 from the top tube filled with conductive fluid to the bottom tube.

TABLE 1

|      | I1 | A1 | A2 | B1 | B2 | C1 | C2 | D1 | D2 | I2 |
|------|----|----|----|----|----|----|----|----|----|----|
| S1   | −  | 0  | 0  | 1  | 1  | 0  | 0  | 1  | 1  | 0  |
| *S2  | 0  | 0  | 0  | 1  | 1  | 0  | 0  | 1  | 1  | +  |
| S3   | 0  | 0  | 0  | 0  | 0  | 0  | 0  | 1  | 1  | +  |
| S4   | 0  | 1  | 1  | 0  | 0  | 0  | 0  | 1  | 1  | +  |
| *S5  | +  | 1  | 1  | 0  | 0  | 0  | 0  | 1  | 1  | 0  |
| S6   | +  | 1  | 1  | 0  | 0  | 0  | 0  | 0  | 0  | 0  |
| S7   | +  | 1  | 1  | 0  | 0  | 1  | 1  | 0  | 0  | 0  |
| *S8  | 0  | 1  | 1  | 0  | 0  | 1  | 1  | 0  | 0  | −  |
| S9   | 0  | 0  | 0  | 0  | 0  | 1  | 1  | 0  | 0  | −  |
| S10  | 0  | 0  | 0  | 1  | 1  | 1  | 1  | 0  | 0  | −  |
| *S11 | −  | 0  | 0  | 1  | 1  | 1  | 1  | 0  | 0  | 0  |
| S12  | −  | 0  | 0  | 1  | 1  | 0  | 0  | 0  | 0  | 0  |

Figure 3A:
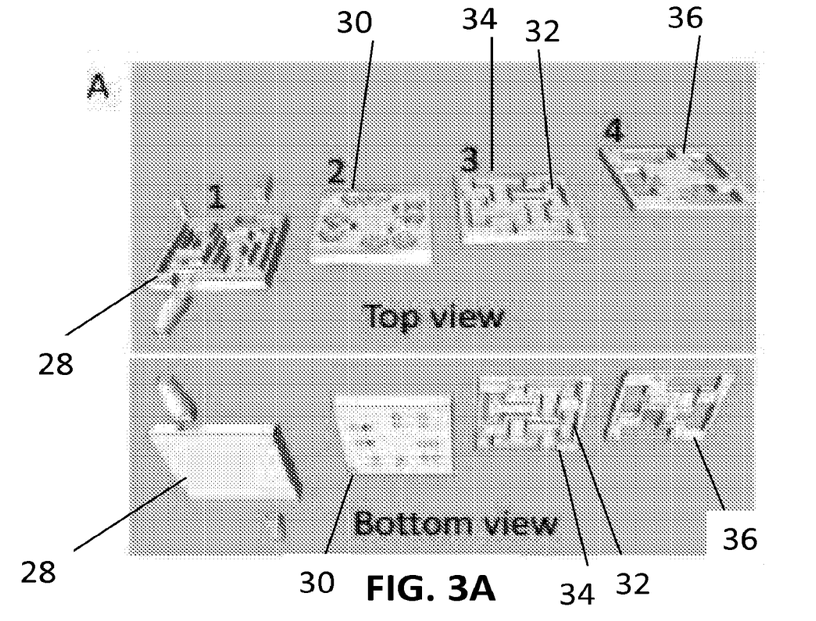
FIG. 3A illustrates the layer components for construction of the system described in FIG. 2 according to an embodiment of the present invention.
Figure 3B:
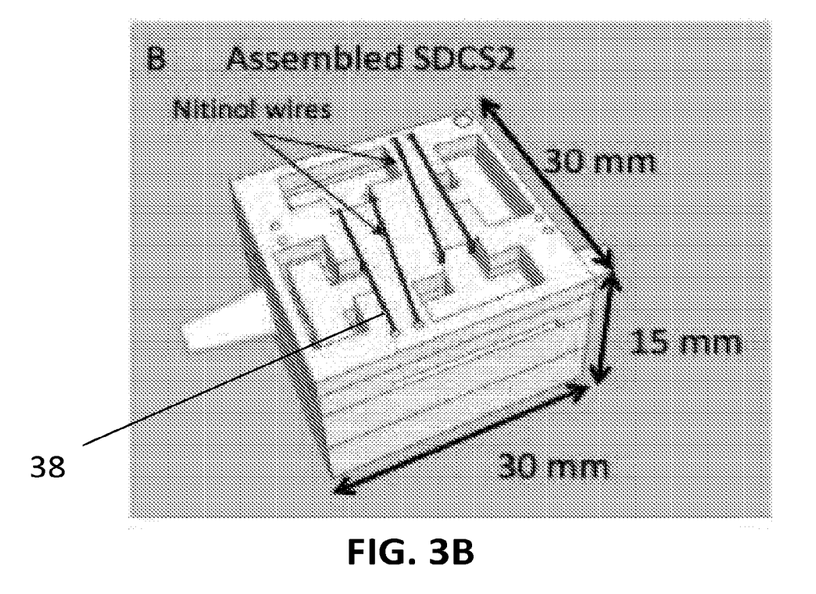
FIG. 3B illustrates the components of the system illustrated in FIG. 3A assembled into the finished device.
Figure 3C:
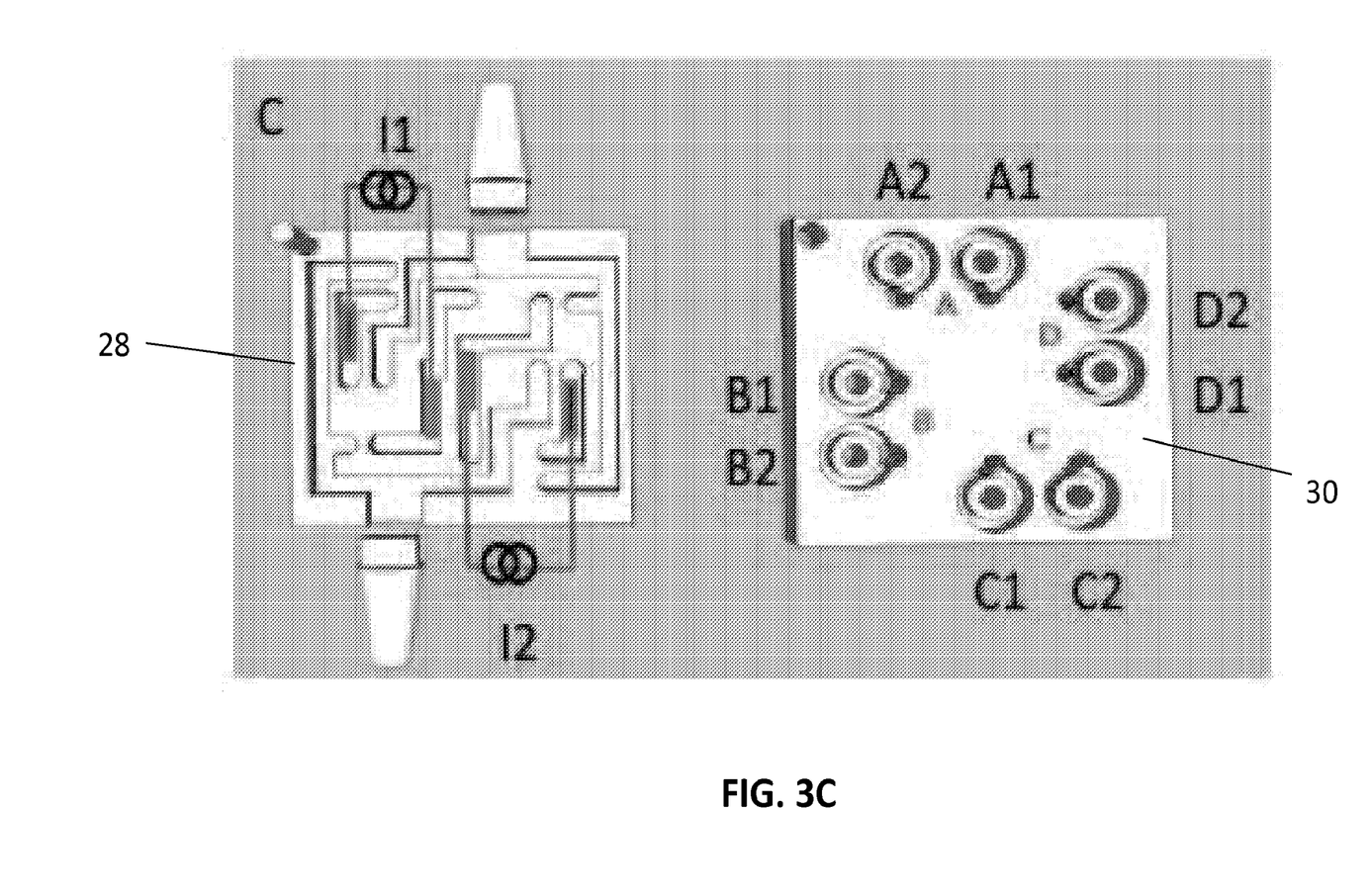
FIG. 3C illustrates the location of the four metal electrodes relative to the other components of the device.

Although the device indicated by the FIG. 2 schematic can be built using different methodologies, FIG. 3A illustrates one embodiment of the device and components for the construction of the present invention. FIG. 3B illustrates the components of the device illustrated in FIG. 3A assembled into the finished device, and FIG. 3C illustrates the location of the electrodes relative to the other components of the device. As illustrated in FIGS. 3A and 3C, layer 1, 28, includes electrodes 18, 20, 22, and 24, and channels through which the current can flow through a saline solution. The channels correspond to those shown in FIG. 2. Layer 1 channels are filled with saline or an ionic hydrogel (such as based on Agar or gelatin) to conduct ionic current. Layer 2, 30, protects and covers layer 1, 28, and provides valve openings for the valves A1, A2, B1, B2, C1, C2, D1, and D2 to connect/disconnect the ionic current in the layer 1 channels. A thin layer of silicone, not shown, is used to cover layer 2, 30, to insulate the saline/gel in the valves from valve plungers 32. Layer 3, 34, and layer 4, 36 include the valve plungers and Nitinol wires 38 used to actuate the valves. Each of the Nitinol wires 38 actuates one pair of valves. All of the layers are formed from plastic or any other suitable material and glued together with water resistant glue, sealer, or other suitable adhesive.

Further, as illustrated in FIG. 3B, the valves are driven by the Nitinol wires 38. When electrically activated, using a microcontroller controlled electronic circuit, described further herein, the Nitinol wires decrease in length by 5%, allowing the intended valve to open. Each Nitinol wire 38 drives a pair of valve actuators, A, B, C, and D. The valve opens when the normally-closed actuator is deformed by tension applied to it through the 100 μm diameter Nitinol wire. The wire is shortened in length, when heated to 70-90° C. by driving 180 mA through the wire. The plunger 32 returns to its original position and lengthens the wire back to the original length when the current is off. The wire can undergo extraction-contraction cycles at up to 2 Hz.

Figure 4:
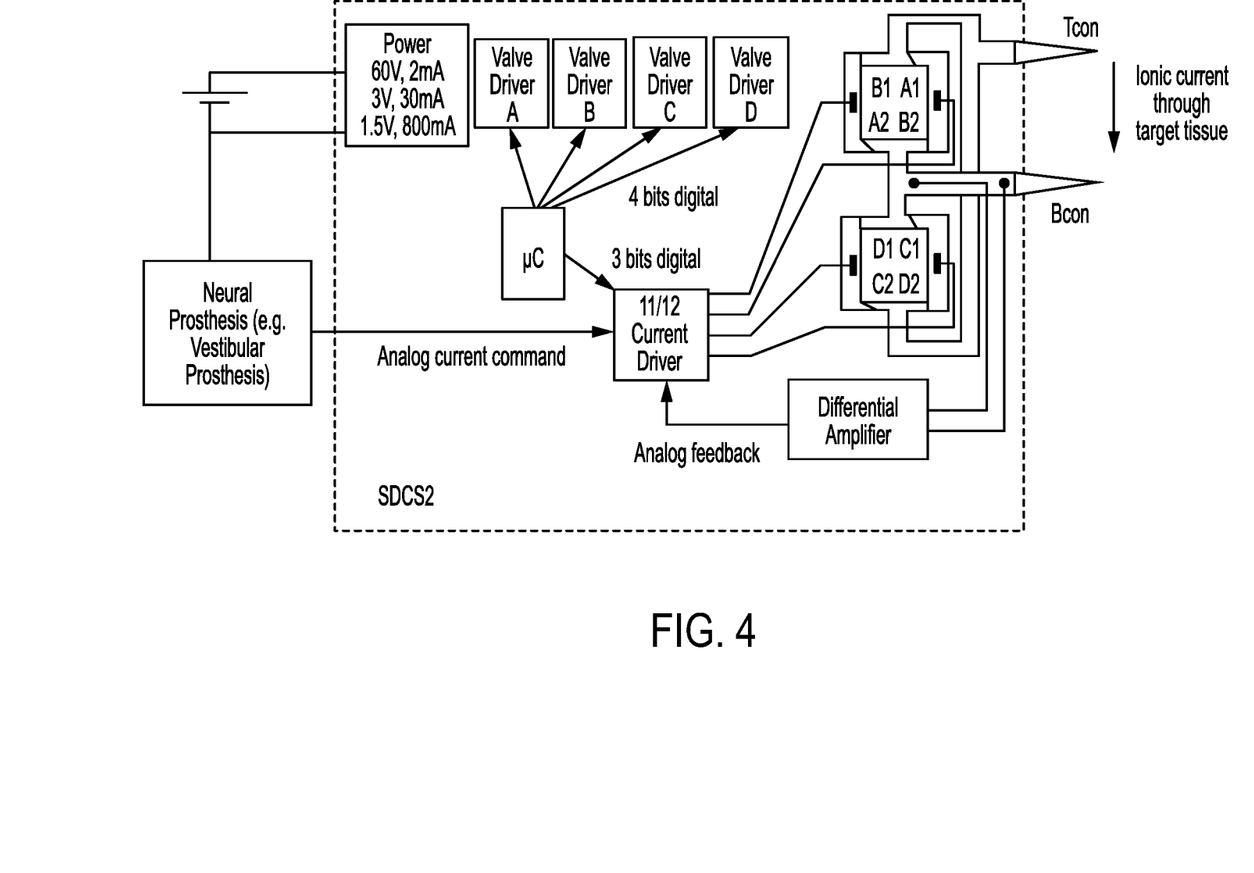
FIG. 4 illustrates a block diagram of electronics for the device, according to an embodiment of the present invention.

FIG. 4 illustrates a block diagram of electronics for the device, according to an embodiment of the present invention. A power block generates three power outputs. The first power output is 60V, 2 mA to drive the current sources I1 and I2. The second is 3V, 30 mA to support the electronics. The third is 1.5V, 800 mA used to drive the Nitinol actuators. The valve drivers A, B, C, D maintain the current through the corresponding Nitinol actuators. I1/I2 Current driver can direct current in either positive or negative direction through the corresponding pairs of electrodes. The differential amplifier detects the ion flow directed through the tissue and sends the proportional voltage signal to the I1/I2 current driver to control the output of the current source. The microcontroller (μC) controls the state machine of the device as indicated by Table 1.

Figure 5:
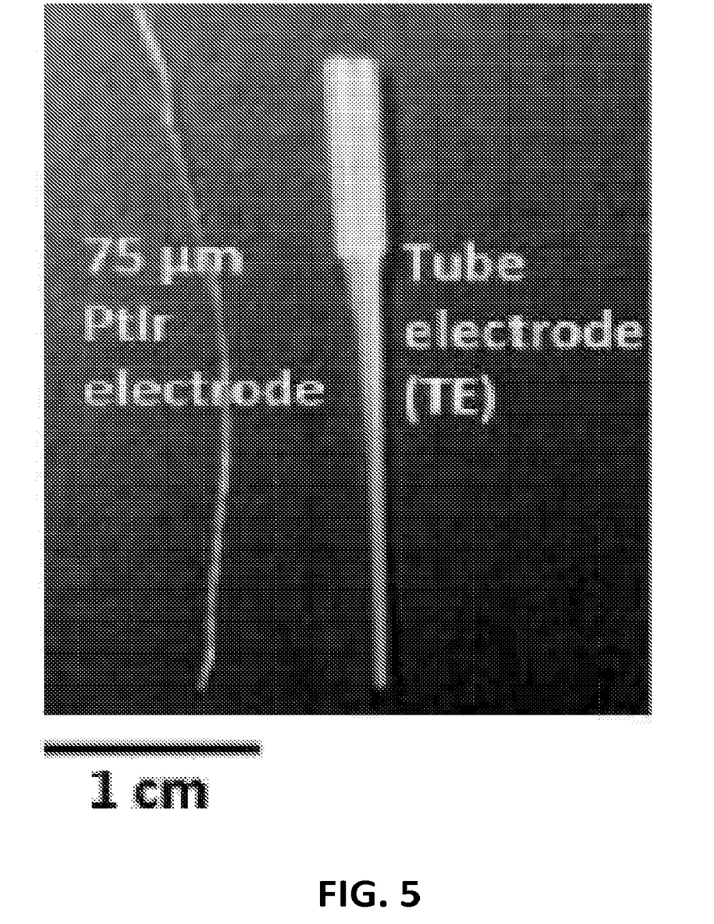
FIG. 5 illustrates one of the two tube conductors (Tube electrode (TE)) used to deliver the ionic current from the device to the neural tissue, according to an embodiment of the present invention.

Two tube electrodes (conductors) are used, as illustrated in FIG. 5 to carry the direct ionic current from the device to the stimulated tissue. This figure shows the one such embodiment of the tube electrodes compared to a typical PtIr wire electrode used in neural stimulation. These tube conductors can be prepared by filling (TE) Eppendorf 20 μL capillary tubes (0.25 mm OD, 0.2 mm ID) with a sterile mixture of agar and ionic solution. While the gel freely conducts the ionic current, it resists fluid motion in and out of the tube and it offers a physical barrier to biological contamination of the implanted tissue.

Far reaching plans to advance safe DC stimulation include use of ionic diodes or ionic transistors that could modulate ionic conductance to control ionic current flow instead of mechanical valves. The ionic diode technology is quickly evolving to create semi-permeable membranes that are constructed to allow flow of ions in one direction but block the flow in the opposite direction. Because mechanical valves are the highest power consuming elements in the SDCS, using ionic diodes that consume no power at all will significantly reduce power of the overall safe DC system. Ionic diodes can be used instead of the valves in the safe DC system construction in a way that is analogous to the use of diodes in a bridge rectifier configuration. A bridge rectifier is a 4-diode electronic component commonly used in power supplies to switch AC to DC power. The ionic diodes will control ion flow instead of electron current flow controlled by conventional diodes.

Assuming the ionic diodes can be reduced in size, more extreme miniaturization of the described technology will also enable multiple stimulation channels to be delivered simultaneously to different stimulation targets because several separate safe DC stimulators could be assembled on one device.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A device for delivering a direct current flow of ions, comprising:
    a conductor filled with a conductive material;
    a first set of two electrodes configured to receive a first alternating current and a second set of two electrodes configured to receive a second alternating current;
    a first set of valves, wherein the first set of valves comprises a first pair and a second pair of valves, said first pair of valves being configured to be in a same first state, and said second pair of valves being configured to be in a same second state opposite to the first state such that when said first pair of valves are both in open state, said second pair of valves are both in closed state and when said first pair of valves are both in closed state, said second pair of valves are both in open state, and
    a second set of valves, wherein the second set of valves comprises a third pair and a fourth pair of valves, said third pair of valves being configured to be in a same third state, and said fourth pair of valves being configured to be in a same fourth state opposite to the third state such that when said third pair of valves are both in open state, said fourth pair of valves are both in closed state and when said third pair of valves are both in closed state, said fourth pair of valves are both in open state,
    wherein the first and second pairs of valves are configured to switch between the open state and the closed state based on said first alternating current applied to said first set of two electrodes to generate the direct current flow of ions within the conductive material;
    wherein the third and fourth pairs of valves are configured to switch between the open state and the closed state based on said second alternating current applied to said second set of two electrodes to generate the direct current flow of ions within the conductive material;
    wherein the conductor filled with the conductive material is configured to direct the direct current flow of ions into a target tissue; and
    wherein the first set of electrodes and the second set of electrodes are configured to operate so as to deliver the direct current flow of ions into the tissue without interruption during valve switching.

2. The device of claim 1 wherein the conductor comprises a tube defining a hollow lumen extending therethrough.

3. The device of claim 2 wherein the hollow lumen of the tube is filled with the conductive material.

4. The device of claim 1 wherein the conductive material is an ionic solution or an ionic hydrogel.

5. The device of claim 1 further comprising a housing.

6. The device of claim 5 wherein the housing comprises layers.

7. The device of claim 6 wherein each one of the layers of the housing contains one of the electrodes and the first set of valves and the second set of valves.

8. The device of claim 1 wherein the valves comprise mechanical valves.

9. The device of claim 8 wherein the mechanical valves comprise Nitinol wire.

10. The device of claim 1 wherein the valves comprise a bridge rectifier.

11. The device of claim 1 wherein the valves comprise an ionic diode.

12. A method for delivering a direct current flow of ions comprising:
    applying a first alternating current to a first set of electrodes immersed in a conductive material;
    applying a second alternating current to a second set of electrodes immersed in the ionic solution;
    switching a first pair of valves and a second pair of valves between an opened and closed state based on said first alternating current applied to the first set of electrodes to generate the direct current flow of ions;
    switching a third pair of valves and a fourth pair of valves between an opened and closed state based on said second alternating current applied to the second set of electrodes to generate the direct current flow of ions; and
    directing the direct current flow of ions into a target tissue without interruption during valve switching.

13. The method of claim 12 wherein the first pair and the second pair of valves are configured to switch between an open position and a closed position in phase with alternating current applied to the first set of electrodes.

14. The method of claim 12 further comprising using a conductor to direct the direct current flow of ions into the target tissue.

15. The method of claim 14 wherein the conductor comprises a tube defining an elongate inner lumen.

16. The method of claim 15 wherein the elongate inner lumen of the tube is filled with the conductive material.

17. The method of claim 16 wherein the conductive material is an ionic solution or an ionic hydrogel.

18. The method of claim 12 further comprising closing the first pair of valves when the second pair of valves are opened, and opening the first pair of valves when the second pair of valves are closed.

19. The method of claim 12 further comprising closing the third pair of valves when the fourth pair of valves are opened, and opening the third pair of valves when the fourth pair of valves are closed.

* * * * *